(12) United States Patent
Sato et al.

(10) Patent No.: US 7,442,809 B2
(45) Date of Patent: Oct. 28, 2008

(54) METHOD FOR PRODUCING 1,3-DIOXOLAN-4,6-DIONE COMPOUND

(75) Inventors: Shingo Sato, Kanagawa (JP); Hideto Mori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/628,338

(22) PCT Filed: May 31, 2005

(86) PCT No.: PCT/JP2005/010302

§ 371 (c)(1),
(2), (4) Date: Dec. 4, 2006

(87) PCT Pub. No.: WO2005/118566

PCT Pub. Date: Dec. 15, 2005

(65) Prior Publication Data

US 2008/0015365 A1    Jan. 17, 2008

(30) Foreign Application Priority Data

Jun. 4, 2004    (JP) .............................. 2004-166665

(51) Int. Cl.
C07D 319/04    (2006.01)
C07D 317/72    (2006.01)
(52) U.S. Cl. ...................... 549/274; 549/265
(58) Field of Classification Search ................ 549/274, 549/282, 283, 265
See application file for complete search history.

(56) References Cited

FOREIGN PATENT DOCUMENTS

| JP | 62-4282 A | 1/1987 |
|---|---|---|
| JP | 1-151573 A | 6/1989 |
| JP | 8-176140 A | 7/1996 |
| JP | 2002-249674 A | 9/2002 |

OTHER PUBLICATIONS

Davidson et al., J. Am. Chem. Soc., 1948, 70, 3426-3428.*
J. Chem. Soc., vol. 93, p. 598, 1908.
J. Am. Chem. Soc., vol. 70, p. 3426, 1948.
Chem. Ber., vol. 94, p. 929, 1961.
Tetrahedron. Left., vol. 30, p. 5281, 1989.
Kozlov, N. G. et al., Synthesis of 1-Aryl-3-oxo-1,2,3,4-tetrahydrobenzo [f] quinol ines, Russian Journal of Organic Chemistry, (202), 38 (8), 1166-1170, Compound (II).
Velikorodov, A. V., Reaction N,N'-di (methoxycarbonyl)-p-benzoquinonediimine with Meldrum's acid and its analogs, Russian Journal of Organic Chemistry, May 2004, 40 (5), 690-692.
Eistert, Bernd et al., Experiments with "Meldrum's acid" and other cyclic esters (acylals) of malonic acids, Chemische Berichte, 1961, 94, 929-947.
Love, Bernard et al., Malonamic esters. New class of sedative-tranquilizers, Journal of Medicinal Chemistry, 1969, 12 (5), 854-859.

* cited by examiner

*Primary Examiner*—Bernard Dentz
*Assistant Examiner*—David E Gallis
(74) *Attorney, Agent, or Firm*—Sughrue Mion, PLLC

(57) ABSTRACT

A method for producing a 1,3-dioxan-4,6-dione compound from a ketone compound and a malonic acid, the method comprising: precipitating a 1,3-dioxan-4,6-dione compound as a crystal from a mixed solvent comprising a first organic solvent having a dielectric constant of 10 or more and a water, so as to form a precipitated 1,3-dioxan-4,6-dione compound; and isolating the precipitated 1,3-dioxan-4,6-dione compound by a solid-liquid separation.

7 Claims, No Drawings

METHOD FOR PRODUCING 1,3-DIOXOLAN-4,6-DIONE COMPOUND

TECHNICAL FIELD

This invention relates to a method for producing 1,3-dioxan-4,6-dione compounds which are useful as materials for synthesizing, for example, physiologically active natural compounds, medicines and agricultural chemicals, pigments, functional materials and the like.

BACKGROUND ART 1,3-Dioxan-4,6-dione compounds are a kind of active methylene compounds, which are compounds useful as materials for synthesizing physiologically active natural compounds, medicines and agricultural chemicals, pigments, functional materials and the like.

Particularly, a 1,3-dioxan-4,6-dione compound having dimethyl group at the 2-position is called Meldrum's acid, can be produced by allowing acetone and malonic acid to undergo the reaction in acetic anhydride in the presence of a catalytically effective amount of sulfuric acid (*J. Chem. Soc.*, vol. 93, p. 598, 1908 and *J. Am. Chem. Soc.*, vol. 70, p. 3426, 1948) and is also on the market.

General 1,3-dioxan-4,6-dione compounds can be synthesized in accordance with the methods described in *Chem. Ber.*, vol. 94, p. 929, 1961 and *Tetrahedron Lett.*, vol. 30, p. 5281, 1989. In addition, a method for producing a 1,3-dioxan-4,6-dione compound derived from cyclohexanone and malonic acid is also related (JP-A-2002-249674).

DISCLOSURE OF THE INVENTION

According to the examinations carried out by the present inventors, it was revealed that the problems in producing a 1,3-dioxan-4,6-dione compound are the method for taking out the product and the reduction of reactivity when structure of the ketone compound to be used in the reaction was changed.

For example, in the method described in JP-A-2002-249674, the product is precipitated as crystals by adding the reaction liquid to a mixed system comprising hexane/water, and this is isolated by a solid-liquid separation, but since the hexane/water has a property to separate into two layers, the product is apt to solidify via the oil emulsified from around the interface, thus posing a disadvantage in that impurities are apt to be incorporated.

It was found that, since the effect of water and hexane to wash the crystals isolated by a solid-liquid separation is also poor, acid components are apt to remain in the obtained 1,3-dioxan-4,6-dione compound and become a cause of deterioration of the product of interest.

Also, since hexane hardly has electric conductivity, there is a possibility of spoiling safety in terms of explosion protection in the industrial scale production.

In addition, since the reactivity is reduced in many cases when structure of the ketone compound to be used in the reaction is changed, there is another problem in that it cannot be generally used. The reactivity is particularly low when a diketone compound is used; for example, even when cyclohexane-1,4-dione and malonic acid are allowed to react with each other within the range of from 0° C. to room temperature for 48 hours, the product of interest can be obtained only with a yield of about 15% (the following reaction scheme).

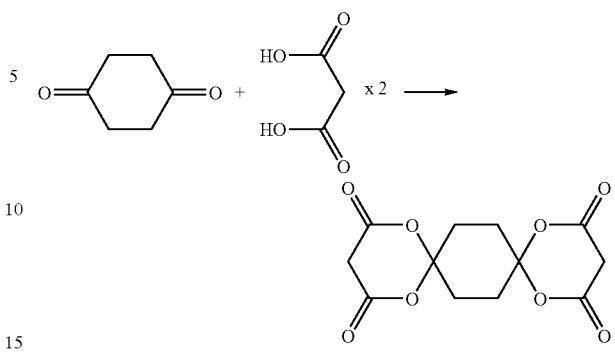

Thus, when isolation and purification of the product of interest, safety, quality ensuring of the product of interest, required period of time, flexibility and the like are taken into consideration, the methods which have so far been reported cannot be regarded as advantageous methods by no means, so that great concern has been directed toward techniques by which a high purity 1,3-dioxan-4,6-dione compound can be produced in a large amount by a convenient process.

Accordingly, the object of the invention is to provide a method for producing 1,3-dioxan-4,6-dione compounds, which can be carried out conveniently and safely at an industrial scale.

Taking the aforementioned circumstances into consideration, the present inventors have conducted intensive studies on the production method of 1,3-dioxan-4,6-dione compounds and found as a result that, in producing a 1,3-dioxan-4,6-dione compound from a ketone compound and malonic acid, the product of interest can be obtained conveniently, safely and stably by precipitating the product as crystals from a specified mixed solvent and isolating this by a solid-liquid separation, thus resulting in the accomplishment of the invention.

The aforementioned problems were solved preferably by the following means.

(1) A method for producing a 1,3-dioxan-4,6-dione compound from a ketone compound and a malonic acid, the method comprising:

precipitating a 1,3-dioxan-4,6-dione compound as a crystal from a mixed solvent comprising a first organic solvent having a dielectric constant of 10 or more and a water, so as to form a precipitated 1,3-dioxan-4,6-dione compound; and isolating the precipitated 1,3-dioxan-4,6-dione compound by a solid-liquid separation.

(2) The method as described in (1) above, wherein a second organic solvent is added to a reaction mixture of the ketone compound and the malonic acid, and the mixed solvent is used after an extraction with the second organic solvent and a concentration.

(3) The method as described in (1) or (2) above, wherein the first organic solvent having a dielectric constant of 10 or more is an alcohol solvent having from 1 to 6 carbon atoms.

(4) The method as described in any of (1) to (3) above, wherein the first organic solvent having a dielectric constant of 10 or more is at least one selected from the group consisting of methanol, ethanol, 1-propanol, 2-propanol, 1-butanol, 2-butanol, 2-methyl-2-propanol, 1-pentanol, 1-hexanol, ethylene glycol, glycerol, propylene glycol, 2-methoxy-1-propanol, 1,3-propanediol, 1,4-butanediol, 1,5-pentanediol and 1,6-hexanediol.

BEST MODE FOR CARRYING OUT THE INVENTION

Production conditions of the invention are described in the following in detail. The invention relates to a method for producing a 1,3-dioxan-4,6-dione compound from a ketone compound and malonic acid.

According to the production method of the invention, not only acetone and the like ketone compounds conventionally known to have high reactivity, but also methyl isobutyl ketone, 2-pentanone, cyclopentenone, cyclohexanone, adamantanone, cyclooctanone, ethyl levulinate, cyclohexane-1,4-dione, pinacolone (t-butyl methyl ketone), acetophenone and the like ketones having relatively low reactivity can also be suitably used by employing desirable reaction conditions.

Molar ratio of malonic acid to be used in the reaction is within the range of from 0.5 to 10.0 moles based on the ketone compound, but its use in excess amount does not exert influence upon the improvement of formation ratio/formation rate of the product of interest to that extent. On the contrary, when malonic acid is used in a too excess amount, it rather results in the increase of waste quantity and inhibition of crystallization and becomes a hindrance in the case of industrial scale production.

According to the invention, the amount of malonic acid is preferably from 0.5 to 5.0 moles, more preferably from 0.5 to 3.0 moles, further preferably from 0.6 to 2.0 moles, based on the ketone compound.

In this connection, when the ketone compound to be used in the reaction has two ketone group in the molecule like the case of cyclohexane-1,4-dione, preferred amount of malonic acid to be used becomes twice of the above.

The reaction of a ketone compound with malonic acid is carried out for example by the related method described in above mentioned *J. Am. Chem. Soc.*, vol. 70, p. 3426, 1948, illustratively in acetic anhydride in the presence of a catalytically effective amount of an acid (e.g., concentrated sulfuric acid).

The reaction temperature varies depending on the structure of the material and its concentration at the time of the reaction and is generally within the range of from 0 to 80° C., but when methyl isobutyl ketone, 2-pentanone, cyclopentenone, cyclohexanone, adamantanone, cyclooctanone, ethyl levulinate, cyclohexane-1,4-dione, pinacolone (t-butyl methyl ketone), acetophenone or the like ketone having 5 or more carbon atoms is used, it is desirable to carry out the reaction within the range of from 20 to 70° C.

The reaction time varies depending on the charging amount and reaction temperature, but is generally within the range of from 0.5 to 20 hours, more preferably from 2 to 12 hours.

In addition, an inert atmosphere is not particularly necessary in the reaction process, but the reaction may be carried out in a stream of argon or nitrogen.

Next, isolation method of 1,3-dioxan-4,6-dione compound in the production method of the invention is described.

The invention is characterized in that it comprises a step of precipitating a 1,3-dioxan-4,6-dione compound as crystals from a mixed solvent comprising an organic solvent having a dielectric constant of 10 or more and water, and isolating this by a solid-liquid separation.

Regarding the dielectric constant, there is a description for example on page 501 of Chemical Handbook, Elementary Series II, 3rd revised edition (Maruzen) edited by The Chemical Society of Japan.

As the organic solvent having a dielectric constant of 10 or more, methanol, ethanol, 2-propanol, 1-butanol and the like alcohol solvents, N,N-dimethylacetamide, N-methylpyrrolidone, sulfolane, dimethyl sulfoxide, N,N,-dimethylimidazolidinone and the like aprotic polar solvents, acetonitrile, nitromethane, pyridine, picoline and the like can be exemplified, but from the cost, easy availability, environmental load in treating waste and the like points of view, the organic solvent to be preferably used in the invention is an alcohol solvent having from 1 to 6 carbon atoms.

Illustrative examples of the alcohol solvent having from 1 to 6 carbon atoms to be used in the invention include methanol, ethanol, 1-propanol, 2-propanol, 1-butanol, 2-butanol, 2-methyl-2-propanol, 1-pentanol, 1-hexanol, ethylene glycol, glycerol, propylene glycol, 2-methoxy-1-propanol, 1,3-propanediol, 1,4-butanediol, 1,5-pentanediol, 1,6-hexanediol and the like.

Among these, it is desirable to use methanol, ethanol, 1-propanol, 2-propanol, 1-butanol, 2-butanol, 2-methyl-2-propanol, 1-pentanol, ethylene glycol, propylene glycol or 2-methoxy-1-propanol, more preferably methanol, ethanol, 1-propanol, 2-propanol, 2-butanol, 2-methyl-2-propanol or 2-methoxy-1-propanol, further preferably methanol, ethanol, 2-propanol or 2-methoxy-1-propanol.

These alcohol solvents may be used as a combination of two or more.

Mixing ratio of the organic solvent and water to be used in precipitating the 1,3-dioxan-4,6-dione compound is optional, with the proviso that it does not cause a problem in operating the process and does not accelerate degradation of the product of interest, but the organic solvent/water mixing ratio (volume ratio) is preferably from 10/1 to 1/20, more preferably from 10/1 to 1/10, and when 2-propanol is used as the organic solvent for example, the organic solvent/water mixing ratio (volume ratio) is from 5/1 to 1/20, preferably from 4/1 to 1/4.

By adding the reaction mixture after the reaction of a ketone compound with malonic acid to the mixed solvent comprising the aforementioned organic solvent and water, the 1,3-dioxan-4,6-dione compound is precipitated as crystals.

As occasion demands, it may be neutralized with sodium hydroxide, potassium hydroxide or the like alkali metal hydroxide. Alternatively, after extraction with an organic solvent, usual post-treatment and subsequent concentration, the residue cam also be precipitated as crystals from the mixed solvent comprising an organic solvent and water. Any solvent can be suitably used as the organic solvent for extraction, with the proviso that it is toluene or the like solvent which is insoluble in water.

Amount of the mixed solvent comprising an organic solvent and water, which is used for effecting precipitation of the 1,3-dioxan-4,6-dione compound as crystals is generally from 3 to 50 volumes based on 1 kg of the 1,3-dioxan-4,6-dione compound, and is preferably from 3 to 20 volumes.

The temperature when crystals are precipitated is 50° C. or less, preferably from 5 to 30° C.

The thus precipitated 1,3-dioxan-4,6-dione compound can be easily isolated by a general solid-liquid separation.

By the use of the production method of the invention described in the above, the use of hexane or the like having a possibility of spoiling safety in terms of explosion protection can be avoided, and the 1,3-dioxan-4,6-dione compound can be obtained conveniently and stably.

In citing a typical example of the illustrative production method, a mixture comprising cyclohexanone, malonic acid, acetic anhydride and a catalytically effective amount of concentrated sulfuric acid is stirred at 40° C.

After cooling of the reaction mixture, this is added to a mixed liquid comprising 2-propanol and water, the mixture is neutralized to pH 3, and the thus precipitated crystals are collected by filtration, washed with 2-propanol and water and then dried, thereby enabling isolation of the 1,3-dioxan-4,6-dione compound of interest. The product obtained in the aforementioned manner has such a high purity that it can be subjected to the following process without carrying out purification.

Typical examples of the 1,3-dioxan-4,6-dione compound preferably produced by the production method of the invention are shown below, though the invention is not limited thereto.

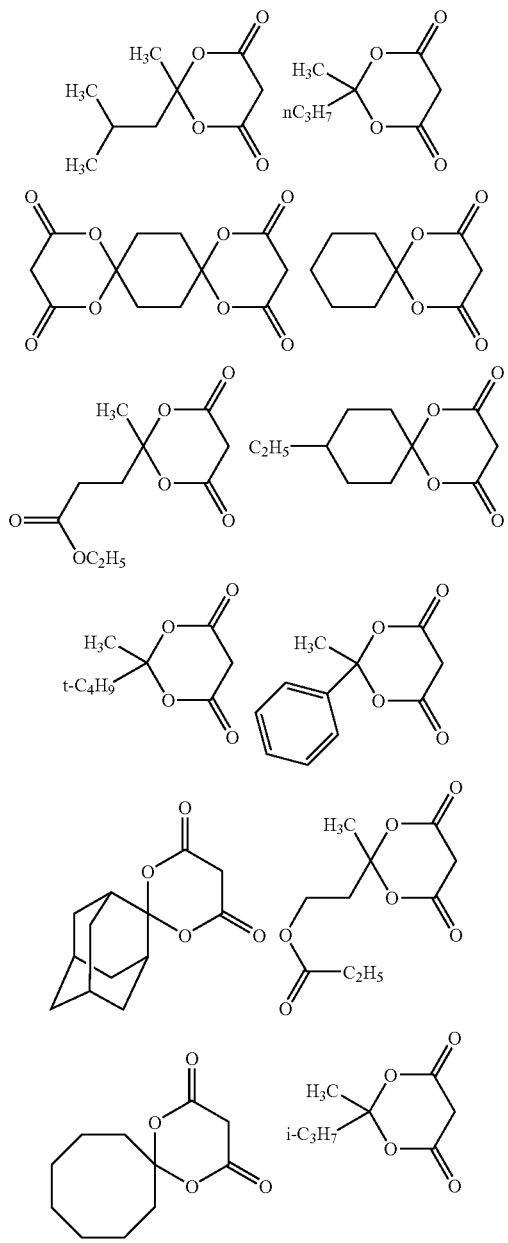

EXAMPLES

The following describes the invention further in detail based on inventive examples and comparative examples, though the invention is not limited thereto.

Inventive Example 1

Synthesis of Compound 1

The reaction scheme is shown below.

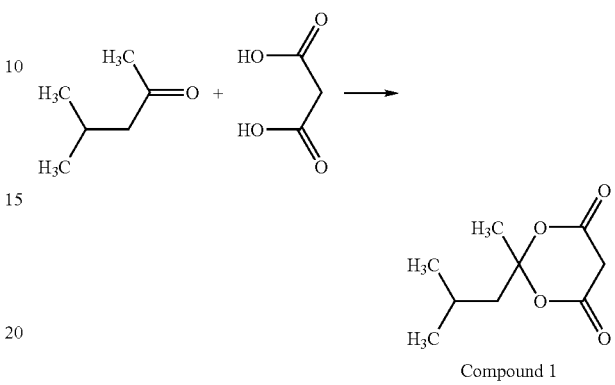

Compound 1

Concentrated sulfuric acid (2 ml) was added to a mixture of acetic anhydride (68.7 g) and malonic acid (50 g), and methyl isobutyl ketone (48.1 g) was subsequently added dropwise thereto at an inner temperature of 30° C. or less. The reaction mixture was stirred at 50° C. for 4 hours, and then toluene (200 ml) and 10% brine (70 ml) were added thereto. The organic layer was fractionated and concentrated, and the residue was crystallized from 2-propanol/water (volume ratio 1/3), filtered and washed using a mixed solution comprising 2-propanol/water (volume ratio 1/3) and then dried to obtain 58.2 g of the compound 1. Yield 65%.

MS: M$^+$186

Inventive Example 2

Synthesis of Compound 2

The reaction scheme is shown below.

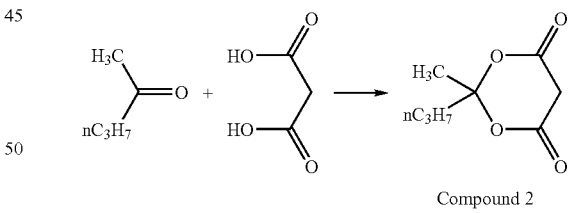

Compound 2

Concentrated sulfuric acid (2 ml) was added to a mixture of acetic anhydride (68.7 g) and malonic acid (50 g), and 2-pentanone (41.4 g) was subsequently added dropwise thereto at an inner temperature of 10° C. or less. The reaction mixture was stirred at 20° C. for 2 hours, and then toluene (200 ml) and 10% brine (70 ml) were added thereto. The organic layer was fractionated and concentrated, and the residue was crystallized from 2-propanol/water (volume ratio 1/3, crystallization temperature 5° C.), filtered and washed using a mixed solution comprising 2-propanol/water (volume ratio 1/3) and then dried to obtain 57.9 g of the compound 2.

Yield 70%.

MS: M$^+$172

Inventive Example 3

Synthesis of Compound 3

The reaction scheme is shown below.

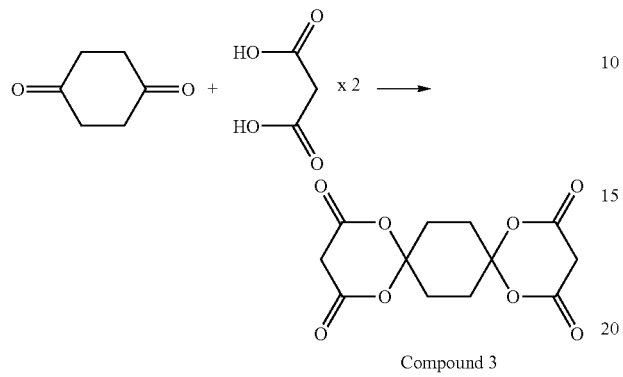

Compound 3

Concentrated sulfuric acid (1 ml) was added to a mixture of acetic anhydride (55 g) and malonic acid (60 g), and cyclohexane-1,4-dione (20 g) was subsequently added thereto in portions at an inner temperature of 30° C. or less. The reaction mixture was stirred at 55° C. for 10 hours, added to a mixed medium comprising 2-propanol (40 ml) and water (80 ml) at 20° C. and then neutralized to pH 4 with a sodium hydroxide aqueous solution. The reaction mixture was stirred at 15° C. for 1 hour, and then the thus precipitated crystals were filtered, washed using a mixed solution comprising 2-propanol/water (volume ratio 1/2) and then dried to obtain 31 g of the compound 3 as pale brown crystals. Yield 61.1%.

MS: $M^+284$

Inventive Example 4

Synthesis of Compound 4

The reaction scheme is shown below.

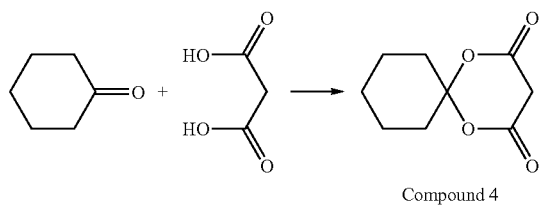

Compound 4

Concentrated sulfuric acid (1 ml) was added to a mixture of acetic anhydride (44 g) and malonic acid (50 g), and cyclohexanone (40 g) was subsequently added dropwise thereto at an inner temperature of 30° C. The reaction mixture was stirred at 40° C. for 5 hours, added to a mixed medium comprising 2-propanol (80 ml) and water (170 ml) at 20° C., and then neutralized to pH 3 with a sodium hydroxide aqueous solution. The reaction mixture was stirred at 20° C. for 1 hour, and then the thus precipitated crystals were filtered, washed with a mixed solution comprising 2-propanol/water (volume ratio 1/2) and then dried to obtain 40.5 g of the compound 4 as ashy white crystals. Yield 54%.

MS: $M^+184$

Inventive Example 5

Synthesis of Compound 5

The reaction scheme is shown below.

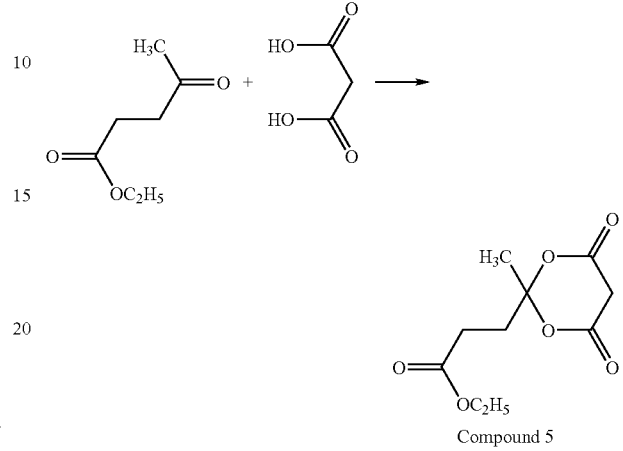

Compound 5

Concentrated sulfuric acid (1 ml) was added to a mixture of acetic anhydride (25.6 g) and malonic acid (18.7 g), and ethyl levulinate (28.9 g) was subsequently added dropwise thereto at an inner temperature of 30° C. or less. The reaction mixture was stirred at 35° C. for 2 hours, and then ethyl acetate (150 ml) and 10% brine (100 ml) were added thereto to fractionate the organic layer. This was washed twice with 10% brine (100 ml), dried with magnesium sulfate and then concentrated, and the residue was crystallized from ethanol/water (volume ratio 1/3, crystallization temperature 5° C.), filtered, washed and then dried to obtain 27.7 g of the compound 5. Yield 63%.

MS: $M^+230$

Comparative Example 1 Synthesis of Compound 3

Cyclohexane-1,4-dione (22.4 g) and malonic acid (41.6 g) were dissolved in acetic anhydride (85 ml), concentrated sulfuric acid (7 ml) was added thereto, and then the reaction mixture was stirred at 5° C. for 36 hours.

Since brown crystals were precipitated as the reaction progressed, they were collected by filtration, washed with cold water and dried to obtain 8.8 g of the compound 3. Yield 15.5%.

Comparative Example 2 Synthesis of Compound 4

Cyclohexanone (43.2 g) and malonic acid (41.6 g) were dissolved in acetic anhydride (50 ml), concentrated sulfuric acid (2 ml) was added thereto, and then the reaction mixture was stirred at room temperature for 18 hours. Water (800 ml) and hexane (600 ml) were added thereto in this order, and the reaction mixture was stirred vigorously at room temperature for 1 hour. The thus precipitated crystals were filtered, washed with water (100 ml) and hexane (100 ml) and then dried to obtain 29.4 g of the compound 4 as a yellowish brown solid. Yield 40%.

From the inventive examples and comparative examples described in the above, it can be understood that the production method of the invention shows good yield and productivity of the product of interest and is also economically advantageous. Thus, superiority and availability of the production method of the invention are obvious.

INDUSTRIAL APPLICABILITY

By the method of the invention, 1,3-dioxan-4,6-dione compounds which are useful as materials for synthesizing, for example, physiologically active natural compounds, medicines and agricultural chemicals, pigments, functional materials and the like can be produced safely and stably.

The entire disclosure of each and every foreign patent application from which the benefit of foreign priority has been claimed in the present application is incorporated herein by reference, as if fully set forth.

The invention claimed is:

1. A method for producing a 1,3-dioxan-4,6-dione compound from a ketone compound and a malonic acid, the method comprising:
    providing a reaction mixture of the ketone compound and the malonic acid, the reaction mixture containing 1,3-dioxan-4,6-dione compound;
    adding a mixed solvent comprising a first organic solvent having a dielectric constant of 10 or more and water, to form a precipitated 1,3-dioxan-4,6-dione compound; and
    isolating the precipitated 1,3-dioxan-4,6-dione compound by a solid-liquid separation,
    wherein the first organic solvent having a dielectric constant of 10 or more is an alcohol solvent having from 1 to 6 carbon atoms.

2. The method according to claim 1, further comprising
    adding a second organic solvent to the reaction mixture of the ketone compound and the malonic acid to extract the 1,3-dioxane-4,6-dione compound, and
    removing the second organic solvent;
    wherein the adding and the removing of the second organic are carried out prior to adding the mixed solvent.

3. The method according to claim 1,
    wherein the first organic solvent having a dielectric constant of 10 or more is at least one selected from the group consisting of methanol, ethanol, 1-propanol, 2-propanol, 1-butanol, 2-butanol, 2-methyl-2-propanol, 1-pentanol, 1-hexanol, ethylene glycol, glycerol, propylene glycol, 2-methoxy-1-propanol, 1,3-propanediol, 1,4-butanediol, 1,5-pentanediol and 1,6-hexanediol.

4. The method according to claim 1,
    wherein the ratio of the first organic solvent and water in the mixed solvent is 10/1 (v/v)-1/20 (v/v) (organic solvent/water).

5. The method according to claim 2,
    wherein the second organic solvent is a solvent insoluble in water.

6. The method according to claim 1,
    wherein an amount of the malonic acid is from 0.6 to 2.0 moles, based on the ketone compound.

7. The method according to claim 1, wherein the 1,3-dioxan-4,6-dione compound is one selected from the group consisting of the following compounds:

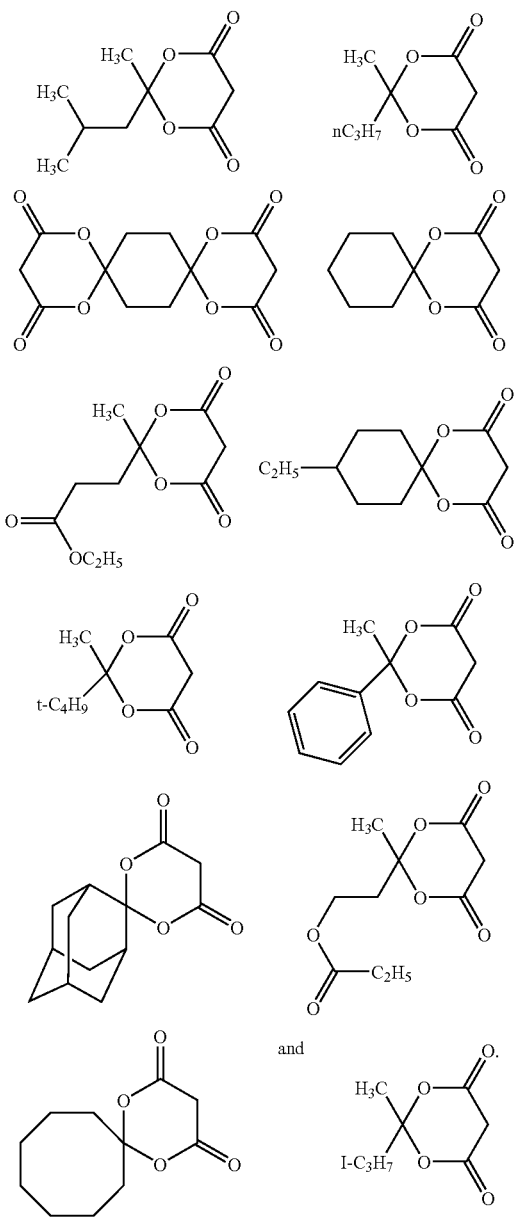

* * * * *